US010238369B2

(12) United States Patent
Guo et al.

(10) Patent No.: US 10,238,369 B2
(45) Date of Patent: Mar. 26, 2019

(54) REAL TIME ULTRASOUND THERMAL DOSE MONITORING SYSTEM FOR TUMOR ABLATION THERAPY

(71) Applicant: The Johns Hopkins University, Baltimore, MD (US)

(72) Inventors: Xiaoyu Guo, Baltimore, MD (US); Emad M. Boctor, Baltimore, MD (US); Dengrong Jiang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 100 days.

(21) Appl. No.: 14/301,037

(22) Filed: Jun. 10, 2014

(65) Prior Publication Data

US 2015/0351724 A1 Dec. 10, 2015

(51) Int. Cl.
*A61B 8/08* (2006.01)
*A61B 5/00* (2006.01)
(Continued)

(52) U.S. Cl.
CPC .......... *A61B 8/5223* (2013.01); *A61B 5/0095* (2013.01); *A61B 8/085* (2013.01);
(Continued)

(58) Field of Classification Search
CPC ......... A61B 8/00; A61B 8/085; A61B 8/5223; A61B 8/0841; A61B 2505/05;
(Continued)

(56) References Cited

U.S. PATENT DOCUMENTS 3,938,372 A * 2/1976 Sproule ................ G01N 29/221
73/633
5,360,268 A * 11/1994 Hayashi ................ G01K 11/22
374/117
(Continued)

FOREIGN PATENT DOCUMENTS

| EP | 1551303 A2 | 7/2005 |
|---|---|---|
| WO | WO-2009/045885 A2 | 4/2009 |
| WO | WO-2011/080713 A1 | 7/2011 |

OTHER PUBLICATIONS

H Chen, G Diebold, "Chemical Generation of Acoustic Waves: A Giant Photoacoustic Effect", Science, 1995, vol. 270, pp. 963-966.*
(Continued)

*Primary Examiner* — Mark Remaly
(74) *Attorney, Agent, or Firm* — Harrity & Harrity, LLP

(57) ABSTRACT

An interventional system with real-time ablation thermal dose monitoring includes an interventional tool, an ultrasound transmitter at least one of attached to or integral with the interventional tool, an ultrasound receiver configured to receive ultrasound signals from the ultrasound transmitter after at least one of transmission through or reflection from a region of tissue while under an ablation procedure and to provide detection signals, and a signal processing system configured to communicate with the ultrasound receiver to receive the detection signals and to calculate, based on the detections signals, a thermal dose delivered to the region of tissue in real time during the ablation procedure.

24 Claims, 4 Drawing Sheets

(51) Int. Cl.
*A61N 7/00* (2006.01)
*A61N 7/02* (2006.01)
*A61B 18/14* (2006.01)
*A61B 18/00* (2006.01)
*A61B 18/26* (2006.01)

(52) U.S. Cl.
CPC .............. *A61B 8/0841* (2013.01); *A61N 7/00* (2013.01); *A61N 7/022* (2013.01); *A61B 18/1492* (2013.01); *A61B 2018/00577* (2013.01); *A61B 2018/263* (2013.01); *A61B 2505/05* (2013.01); *A61N 2007/0004* (2013.01); *A61N 2007/0052* (2013.01)

(58) Field of Classification Search
CPC ...... A61B 2018/00577; A61B 18/1492; A61B 2018/263; A61B 5/0095; A61N 7/022; A61N 7/00; A61N 2007/0052; A61N 2007/0004
See application file for complete search history.

(56) References Cited

U.S. PATENT DOCUMENTS

| | | | | |
|---|---|---|---|---|
| 5,838,000 A * | 11/1998 | Mertesdorf | ............ | B82Y 20/00 250/216 |
| 5,840,023 A | 11/1998 | Oraevsky et al. | | |
| 5,944,687 A | 8/1999 | Benett et al. | | |
| 6,042,556 A * | 3/2000 | Beach | ...................... | A61N 7/02 600/437 |
| 6,623,430 B1 * | 9/2003 | Slayton | .................... | A61B 5/01 600/439 |
| 9,037,217 B1 * | 5/2015 | Peyman | ................. | A61B 18/20 600/427 |
| 2003/0130575 A1 * | 7/2003 | Desai | ................... | A61B 8/0841 600/417 |
| 2007/0016039 A1 * | 1/2007 | Vortman | ................ | A61B 8/467 600/439 |
| 2007/0106157 A1 * | 5/2007 | Kaczkowski | .......... | A61B 5/015 600/438 |
| 2009/0105588 A1 | 4/2009 | Emelianov et al. | | |
| 2012/0108918 A1 * | 5/2012 | Jarvik | .................. | A61B 5/4824 600/301 |
| 2012/0167694 A1 * | 7/2012 | Li | ....................... | G01N 21/1702 73/657 |
| 2013/0102932 A1 * | 4/2013 | Cain | ........................ | A61N 7/00 601/2 |
| 2013/0144165 A1 * | 6/2013 | Ebbini | ................. | A61B 8/4488 600/439 |
| 2013/0190613 A1 * | 7/2013 | Boppart | ............... | A61B 5/0066 600/427 |
| 2014/0024928 A1 | 1/2014 | Boctor et al. | | |
| 2014/0088575 A1 * | 3/2014 | Loeb | ..................... | A61B 18/24 606/7 |
| 2014/0257262 A1 * | 9/2014 | Carpentier | ............... | A61N 7/02 606/28 |
| 2015/0025420 A1 * | 1/2015 | Slayton | .................. | A61B 8/429 601/2 |

OTHER PUBLICATIONS

International Search Report and Written Opinion of the International Searching Authority in PCT International Application No. PCT/US2015/030855 dated Aug. 11, 2015.

Boctor et al., "Three-Dimensional Heat-induced Echo-Strain Imaging for Minitoring Interstitial High Intensity Ablation," The International Society for Optical Engineering (SPIE), 2009, pp. 1-12.

\* cited by examiner

REAL TIME ULTRASOUND THERMAL DOSE MONITORING SYSTEM FOR TUMOR ABLATION THERAPY

GOVERNMENT LICENSE RIGHTS

This invention was made with government support under NIH R21 EB015638 awarded by the National Institutes of Health (NIH). The government has certain rights in the invention.

BACKGROUND

1. Field of Invention

The field of the currently claimed embodiments of this invention relates to thermal dose monitoring systems for tumor ablation therapy, and more particularly to real-time ultrasound thermal dose monitoring systems for tumor ablation therapy.

2. Discussion of Related Art

Tumor ablation therapy is one approach to remove tumor tissue by minimally invasive surgical procedures. In such procedures, an interventional tool is typically directed to a location within the patient's body that is either close to, or within tumor tissue. Energy is then delivered to the tumor tissue with a density and sufficiently rapidly to destroy tumor tissue by ablation. The interventional ablation tool can be a radio frequency ablation tool, or a laser ablation tool, for example. In the tumor ablation treatment, the safety and accuracy could be greatly improved if the operator is able to monitor the thermal dose in real time.

In the tumor ablation operation, applicator guidance and ablation process monitoring are crucial, especially when the operation requires high accuracy. However, due to the low contrast between ablated and untreated tissue in the B mode image, conventional ultrasound imaging is usually not effective for the monitoring. Other imaging modalities including CT and MRI can be incorporated with the ablation therapy and provide effective image guidance and monitoring; however, the requirements of these high-end imaging devices makes this approach unaffordable or inaccessible for many patients. The radiation dose and magnetic field compatibility requirements also prevent these methods from being widely used. Therefore, there remains a need for thermal dose monitoring systems for tumor ablation therapy.

SUMMARY

An interventional system with real-time ablation thermal dose monitoring according to some embodiments of the current invention includes an interventional tool, an ultrasound transmitter at least one of attached to or integral with the interventional tool, an ultrasound receiver configured to receive ultrasound signals from the ultrasound transmitter after at least one of transmission through or reflection from a region of tissue while under an ablation procedure and to provide detection signals, and a signal processing system configured to communicate with the ultrasound receiver to receive the detection signals and to calculate, based on the detections signals, a thermal dose delivered to the region of tissue in real time during the ablation procedure.

An ultrasound transmitter according to some embodiments of the current invention includes a liquid cell, an optical fiber having a transmitting end coupled to the liquid cell such that the transmitting end is fixed with an interior space defined by the liquid cell, and a laser optically coupled to the optical fiber. The liquid cell includes an expandable portion that is free to expand due to thermal expansion and phase change of a fluid when contained within the liquid cell and while the fluid is being exposed to energy from the laser to induce a Giant Photo-Acoustic Effect.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The terms "light" and "optical" are intended to have a broad meaning. They can include, but are not limited to, the visible regions of the electromagnetic spectrum. They can also include nonvisible regions of the electromagnetic spectrum such as infrared and ultraviolet light, as well as visible regions.

The term "photoacoustic" is intended to have a broad definition which can be photons at any energy suitable for the particular application that deposit energy that generates an acoustic signal in a body of interest.

The term "body" refers generally to a mass, and not specifically to a human or animal body. In some applications, the body of interest can be a human or animal organ, or a portion thereof.

The term "interstitial" means to be inserted into tissue, such as, but not limited to, a needle inserted into tissue with the inserted tip being surrounded by the tissue.

Some embodiments of the current invention can provide a high-accuracy, real-time ultrasound thermal dose monitoring system for tumor ablation therapy. The following describes several different thermal dose monitoring systems and methods based on the ultrasound imaging modality to help the operator control the treatment process. One or multiple of these methods can be implemented in a tumor ablation system to provide a low cost, zero radiation dose, real-time, high-accuracy guidance and monitoring solution for HIFU ablation therapy, thus reducing the risk and difficulty of the operation. However, the broad concepts of the current invention are not limited to such a system.

Some embodiment of the current invention can provide one or more of the following:

1) A new configuration of ultrasound imaging system: ablation applicator with ultrasound elements (PZT or photoacoustic) implemented to generate imaging pulses and an external transducer array to receive the signal.
2) Intra-ablation region acoustic radiation force imaging (ARFI). The ARF pulses can be generated by the same transducer that can be attached to the ablation applicator. The image can be reconstructed by a synchronized ultrasound imaging array.
3) New imaging reconstruction algorithms based on the novel imaging methods.

Figure 1:
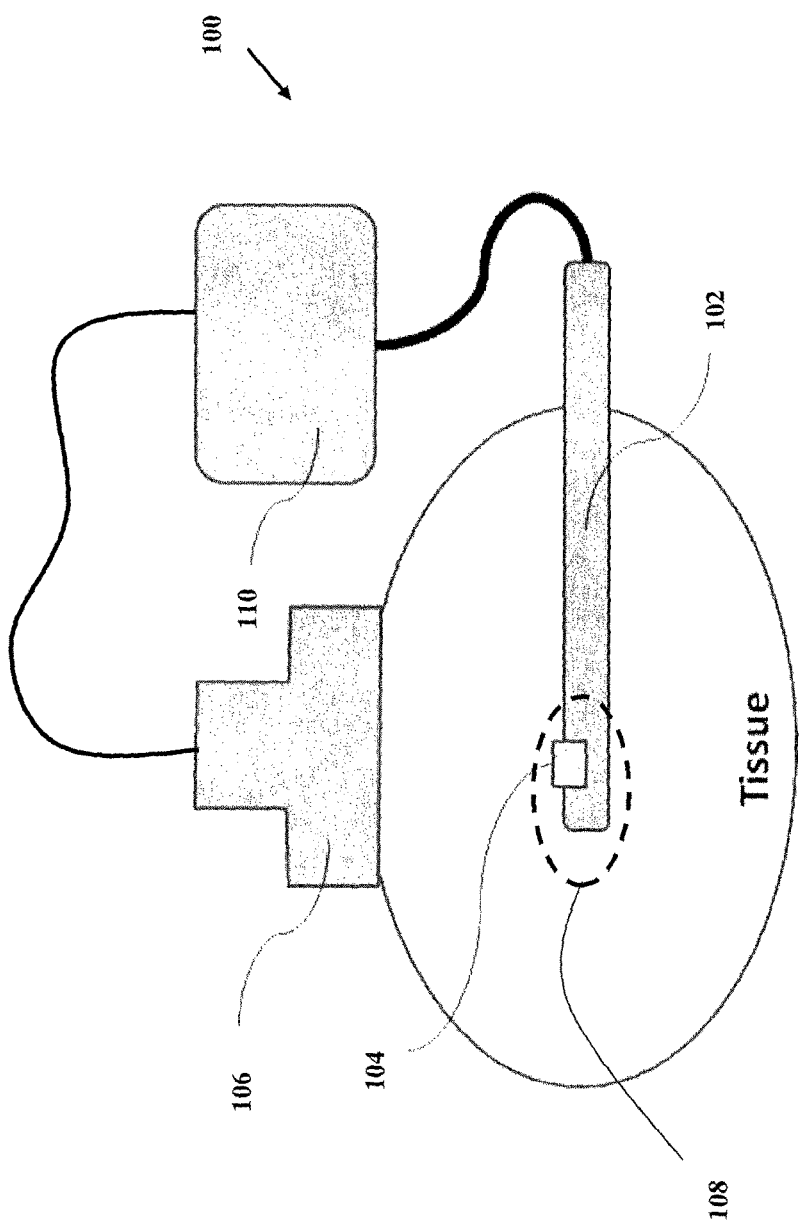
FIG. 1 is a schematic illustration of an interventional system with real-time ablation thermal dose monitoring according to an embodiment of the current invention.

FIG. 1 provides a schematic illustration of an interventional system 100 with real-time ablation thermal dose monitoring according to an embodiment of the current invention. The interventional system 100 includes an interventional tool 102, an ultrasound transmitter 104 at least one of attached to or integral with the interventional tool 102, an ultrasound receiver 106 configured to receive ultrasound signals from the ultrasound transmitter 104 after at least one of transmission through or reflection from a region of tissue 108 while undergoing an ablation procedure and to provide detection signals, and a signal processing system 110 configured to communicate with the ultrasound receiver 106 to receive the detection signals and to calculate, based on said detections signals, a thermal dose delivered to said region of tissue 108 in real time during said ablation procedure.

In FIG. 1, the ultrasound receiver 106 is incorporated into an ultrasound probe, such as a manually operable ultrasound probe. The ultrasound receiver 106 can include an array of receiver elements which can be, but are not limited to, a phased array of receiver elements. In other embodiments, the ultrasound receiver 106 can be attached to, or integral with, the interventional tool 102 and/or with an additional interventional tool (not shown) to be used in conjunction with the interventional tool 102. For embodiments in which the ultrasound receiver 106 is attached to or integral with the interventional tool 102, the receiver operates in reflection mode. In such embodiments, the ultrasound receiver 106 can be a single element or an array of elements, which can be, but is not limited to, a phased array similar to when it is incorporated into a manually operable ultrasound probe. In some embodiments, the ultrasound receiver 106 and the ultrasound transmitter 104 can share common elements, such as, but not limited to one or more piezoelectric elements that can be used to both transmit and receive ultrasound signals.

The ultrasound transmitter 104 can include, but is not limited to, one or more piezoelectric transducers and/or a photoacoustic transmitter. Furthermore, ultrasound transmitters and receivers described in U.S. patent application Ser. No. 13/943,649 (assigned to the same assignee as the current application) can be used in some embodiments of the current invention. The entire content of U.S. patent application Ser. No. 13/943,649, published as US2014/0024928, is incorporated herein by reference.

In some embodiments, the interventional tool 102 can be an interventional ablation tool. In other embodiments, the interventional tool 102 can be an interventional tool adapted to be used in conjunction with an interventional ablation tool. In embodiments in which the interventional tool 102 is an interventional ablation tool, the interventional ablation tool can be, but is not limited to, at least one of a radio frequency, laser, high-intensity focused ultrasound (HIFU), or thermal ablation tool.

In some embodiments in which the interventional tool 102 is an interventional ablation tool, the ultrasound transmitter 104 can also be used to provide ablation in addition to ultrasound imaging signals, for example by high-intensity focused ultrasound.

When using a photoacoustic transmitter in the ultrasound transmitter 104, it is desirable to achieve a higher optical-to-acoustical conversion efficiency. However, in the conventional photoacoustic effect, the conversion is done through photo-thermal expansion, which has a low conversion efficiency. The Giant Photoacoustic Effect has a much higher efficiency since the conversion is done through the target material undergoing a phase change. The Giant PA effect was first discovered by H. Chen and G. Diebold in 1995. In contrast to the conventional PA effect in which optical-acoustic conversion is through the photo-thermal expansion of the material, the Giant PA requires a much higher optical power density such that the target material, liquid in most cases, is superheated within nanoseconds. The rapid phase change causes a local cavitation effect, and the thermal energy is converted to acoustic energy during the cavity expansion. In some liquids, such as carbon-particle suspensions, high temperature chemical reactions also contribute to the PA process. The acoustic generation in this process has been proven to be a 2 to 3 orders of magnitude more efficient than conventional PA.

Figure 2:
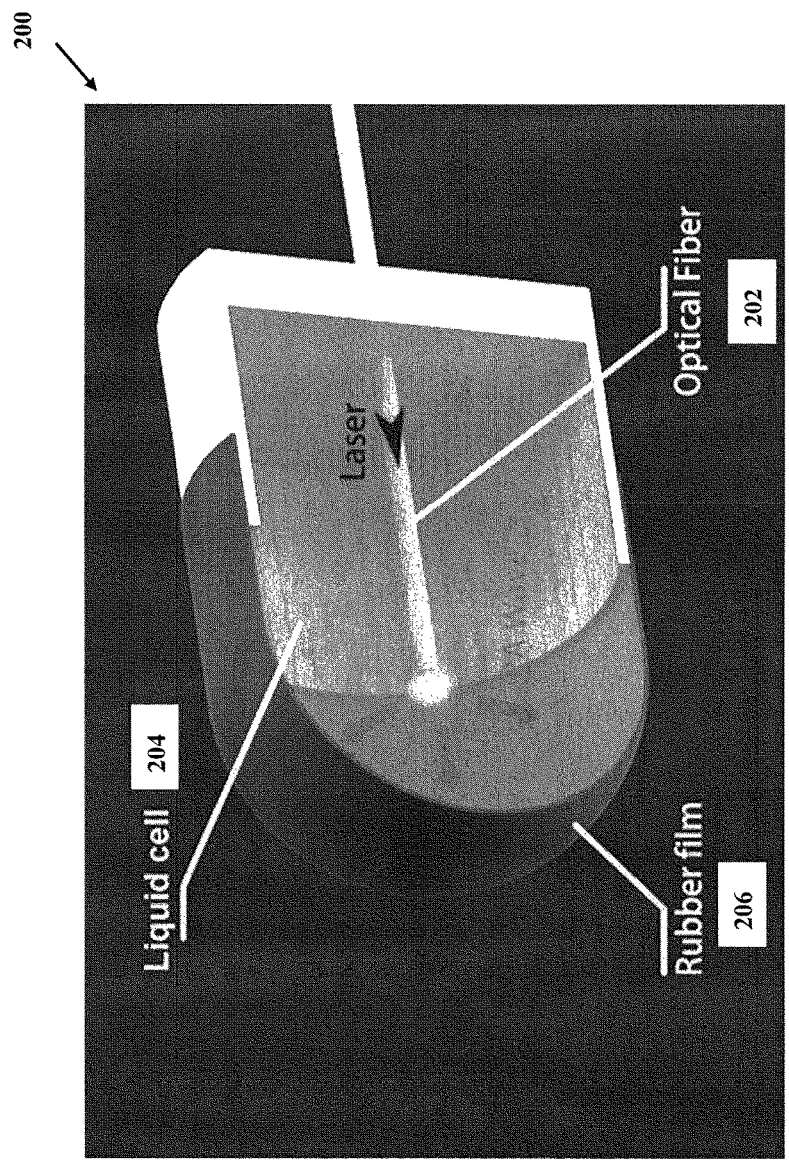
FIG. 2 is a schematic illustration of a photoacoustic ultrasound transmitter according to an embodiment of the current invention.

FIG. 2 provides a schematic illustration of an ultrasound transmitter 200 according to an embodiment of the current invention. The ultrasound transmitter 200 includes a laser, not shown in FIG. 2, optically coupled to an optical fiber 202. The optical fiber 202 has a transmitting end that is fixed in a liquid cell 204. The liquid cell 204 is structured to contain a liquid therein. The liquid cell 204 has an expandable portion 206 that is suitable to expand when liquid contained within liquid cell 204 undergoes thermal expansion and expansion due to a phase change, such as liquid to gas, to utilize the Giant PA Effect. In the example of FIG. 2, the expandable portion 206 is a rubber film attached to a rigid base structure. However, the general concepts of the current invention are not limited to only rubber films. The liquid cell can contain a fluid comprising one or more liquids, gases and/or particles in a suspension. The fluid can be selected according to its thermal expansion, thermal absorption and phase change properties according to the particular application. As shown in the FIG. 2, the ultrasound transmitter 200 has an optical fiber 202 fixed in the liquid cell 204, the laser beam propagates from the fiber tip directly to a liquid with high optical absorption coefficient, thus the laser energy will be absorbed within a very small range. When the energy density is high enough to induce overheated liquid, an instantaneous liquid volume expansion will cause a strong acoustic pulse generation.

Method 1: Reconstruct the Hot Region Image by Tracking the Time of Flight.

In an embodiment of the current invention, the signal processing system 110 is configured to calculate the thermal dose delivered to the region of tissue 108 in real time based on time of flight measurements of ultrasound signals from the ultrasound transmitter 104 that pass through regions undergoing ablation as well as regions immediately surrounding the regions undergoing ablation.

This embodiment is based on the fact that the speed of sound in tissue varies with temperature. In this embodiment, the ultrasound transmitter 104 is inserted into the region of tissue 108 with the interventional tool 102, which can be considered to be a modified ablation catheter, which can provide RF, HIFU or thermal ablation, for example. A linear or phased imaging array for the ultrasound receiver 106 works as a passive detector outside the organ or body. Imaging ultrasound pulses are generated by the internal source 104 and received by the array 106. During the ablation process, the interventional tool 102 creates a hot region which has a higher speed of sound than that of the surrounding tissue. The variation in the speed of sound changes the impulse response of the firing-receiving system. The phase, amplitude and propagation time of the ultrasound pulse are recorded by the imaging array to reconstruct the image of the hot region.

Figure 3:
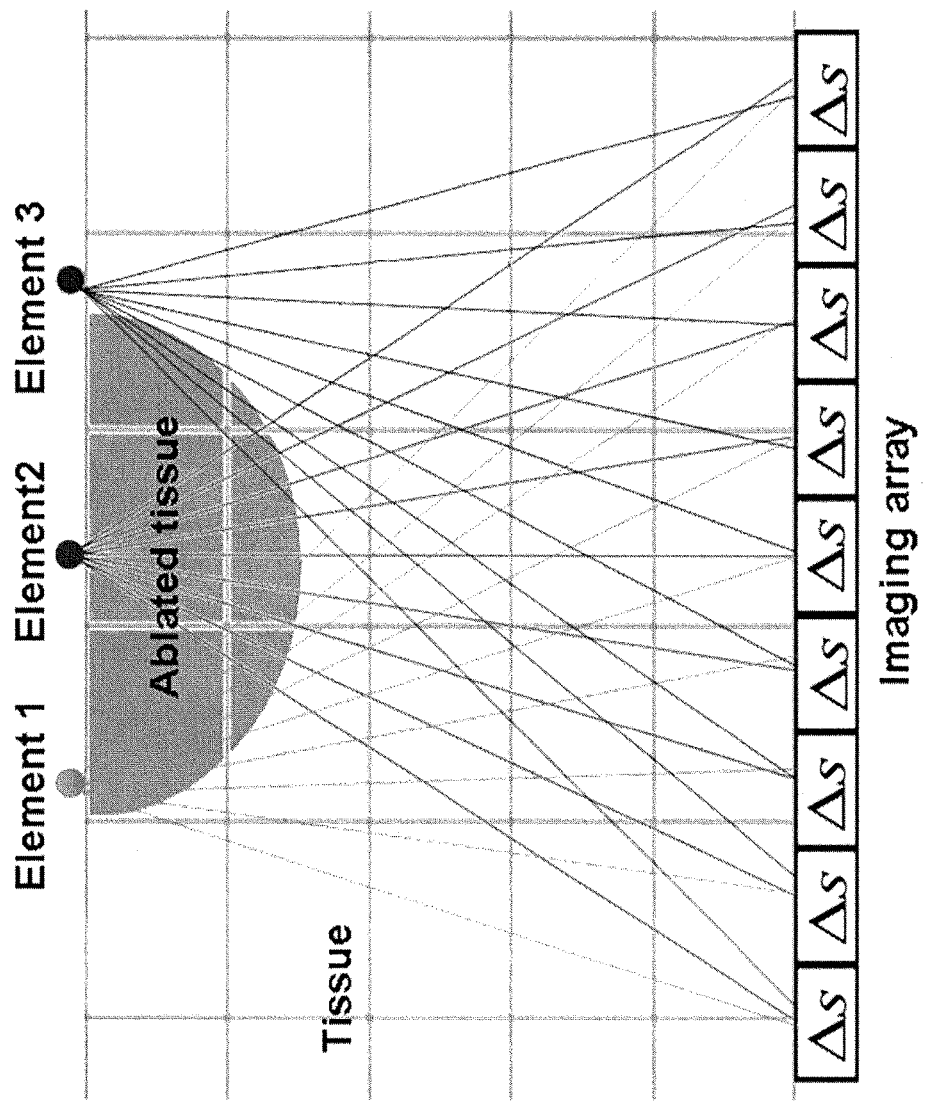
FIG. 3 is a schematic illustration of an example of a configuration of temperature map reconstruction using internal ultrasound sources according to an embodiment of the current invention. Elements 1, 2, 3 (not limited to 3, could be 1 to n) can be multiple ultrasound sources integrated on the same interventional tool, or the same source at different location.
Figure 4:
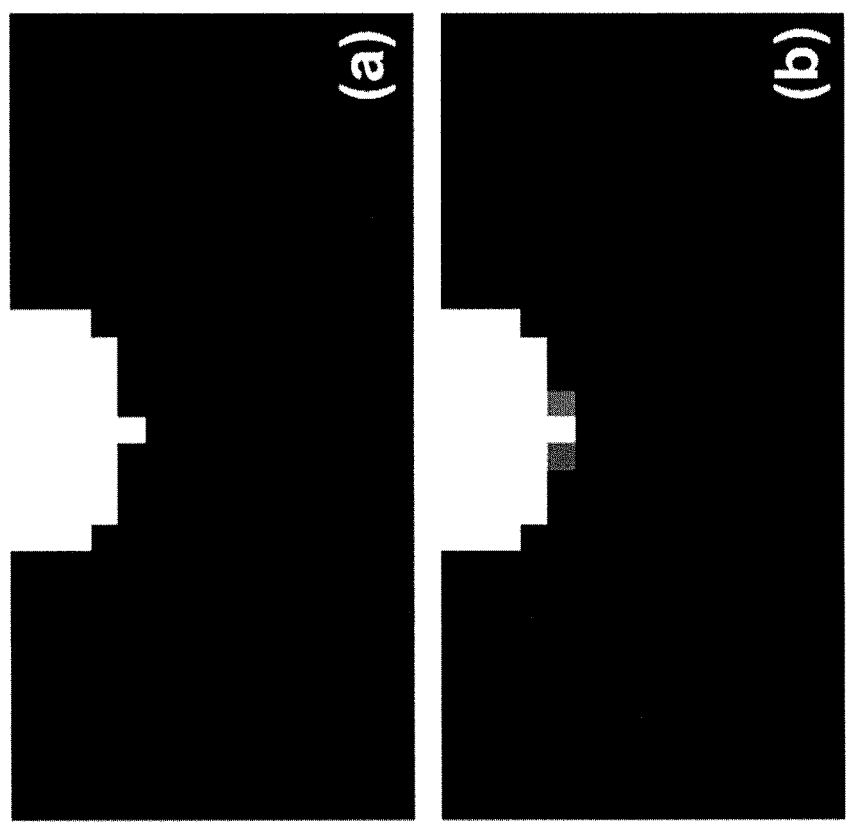
FIG. 4 shows the simulation results of a reconstruction method according to an embodiment of the current invention. A numerical simulation was performed assuming a ROI of 6 cm×3 cm with 2 mm resolution. The ultrasound probe has 128 elements within a total length of 6 cm. The HIFU needle is parallel to the probe. Data was acquired with 30 different transmitter positions evenly distributed in 6 cm. Standard deviation of the uncertainty of transmitter positions was 25 um along both axial and lateral direction. (a) The ground truth with SoS of 1545 m/s in the background and 1570 m/s in the white circle with a radius of 5 cm. (b) Reconstructed SoS map via TV regularization.

In reconstruction, the distance between the internal source 104 and the imaging array 106 is unknown. To map the hot region, several tomographic methods can be used to derive the unknown parameters. One method is to use multiple ultrasound point elements 104. These elements fire ultrasound pulses from different locations, and the spacing between them is known. As a result, the number of independent equations will be more than the number of unknowns, and the reconstruction becomes a solvable problem. Another method is to move the catheter inside the tissue and transmit the ultrasound pulses at different locations. FIG. 3 provides a schematic illustration of such an embodiment of the current invention. FIG. 4 shows the results of a simulation in (b) that closely replicates the ground truth (or actual) feature (a) to be reproduced.

Method 2: Reconstruct the Hot Region Image by Tracking the Echo Pattern Variation from an External Imaging Probe.

In an embodiment of the current invention, the signal processing system 110 is configured to retrieve reference data corresponding to the region of tissue 108 prior to the thermal dose and to calculate the thermal dose delivered to the region of tissue 108 in real time based on a comparison of the reference data to detections signals.

This imaging method is based on the fact that the speed of sound in tissue varies with different temperatures. During the ablation process, the temperature as well as the speed of sound in the tissue near the ablation catheter increases; however, the tissue structure remains the same. So an apparent echo pattern displacement variation can be observed. There are two counteractive effects in the process: local speed increase and thermal expansion due to the increase in temperature. The proportionality between the echo pattern variation and local temperature change is determined by the sound speed-temperature coefficient and tissue thermal expansion coefficient.

The imaging pulse is fired from the ultrasound transducer attached to the ablation catheter. In the interventional HIFU ablation, it could be the same transducer that generates the ablation ultrasound. An external imaging array passively receives the ultrasound pulses. The echo pattern comes from both forward and backward scattering. Reference RF lines are recorded before the ablation process. More RF lines are recorded during the process and compared with the reference to resolve the pattern variation.

Innovative advantages of this method can include the following:
- Compared with the conventional ultrasound echo strain thermal monitoring method, this configuration reduces the motion sensitivity, which is the major obstacle preventing the ultrasound thermal monitoring method from being applied in clinical treatment. Because the imaging ultrasound is from the transducer embedded in the tissue instead of an external imaging array, the timing between the imaging pulse firing and the echo pattern is irrelevant to the position of the external imaging array, so the motion of the external probe does not affect the echo pattern.
- Active-echo tracking is capable of identifying the midplane within few micrometers with respect to the ablation source. Hence, we can easily overcome the motion artifact. This innovative feature can be implemented in several ways including: a) injecting a unique pattern that needs to be replicated before acquiring additional data, b) it can be done by a S/W analyzing the active-echo signal and sending pose information to the user
- The imaging pulses are generated from within, such as the center of, the region of interest (ROI). This configuration results in the ROI illuminated being the strongest ultrasound signal. We can obtain high sensitivity for deep lesions in some embodiments.
- The imaging pulses just travel through the tissue between the ROI to the external probe once. The effective detection depth increases.

Method 3: Reconstruct the Hot Region Image by Tracking the Echo Strain from the Probe Attached to the Interventional Catheter.

Another imaging method that is based on the same principle as described immediately (Method 2) above is the following. In this case, the difference is that the signal is received by the detector attached to the ablation catheter; i.e., the external imaging probe is avoided. The detector could be the same transducer that generates the ultrasound pulse, or a separate signal element transducer, or a multi-element imaging array.

Advantages of this method, compare with Method 2, can include the following:
- All the received echo pulses are from backward scattering. The original imaging pulse will not be received. That improves the system SNR.
- The echo ultrasound only travels in the ROI and thus further improves the signal strength. That makes the tissue thickness irrelevant to the detection. Higher frequency ultrasound pulses can be used to improve the resolution.
- It totally removes the external probe, so the motion effect is further reduced.
- The reference data can be intra-operatively acquired in some embodiment, and/or based on a model, and/or based on pre-operative data.

Method 4: Reconstruct the Hot Region Image by Analyzing the Ringing after the Main Ultrasound Peak, the Receiver is an External Imaging Probe.

In an embodiment of the current invention, the signal processing system 110 is configured to calculate the thermal dose delivered to the region of tissue 108 in real time based on a dispersion of the ultrasound signals from the ultrasound transmitter after at least one of transmission through or reflection from the region of tissue 108.

This imaging method is based on the fact that ablation changes the synthetic acoustic properties of the local tissue. The acoustic properties have correlations with the local temperature distribution. If we consider the tissue as a system, the impulse response of the system changes after the ablation process. If a short ultrasound pulse (with single or a few cycles) is fired from the center of the ROI, the waveform changes during the propagation due to the medium dispersion and lack of homogeneity. The received RF line will show multiple ringing cycles after the main peak. The ringing signal carries the information about the acoustic properties distribution of the tissue. By analyzing the ringing signal we can reconstruct the shape and size of the ablated region.

Method 5: Reconstruct the Hot Region Image by Analyzing the Ringing after the Main Ultrasound Peak; the Receiver being Attached to the Interventional Catheter.

In an embodiment of the current invention, a system similar to that of method 4 except the interventional ablation tool is high-intensity focused ultrasound (HIFU) ablation tool that is further configured to provide acoustic pulses for imaging by an acoustic radiation force (ARF) effect. The signal processing system 110 is configured to calculate the thermal dose delivered to the region of tissue in real time based on the ARF effect.

This imaging method is based on the same principle as method 4. The difference is that the signal is received by the detector attached to the ablation catheter; i.e., the external imaging probe is avoided. Advantaged gained from this configuration can be similar to those of method 3.

Method 6: Reconstruct the Hot Region Image by Photoacoustic Effect, One or Multiple Optical Fibers are Attached to the Interventional Catheter to Deliver the Laser Pulses.

This imaging method is based on the photoacoustic effect. One or multiple optical fibers are attached to the ablation catheter. Non-ionizing nanosecond laser pulses (visible and near infrared) are delivered to the region of interest by optic fibers. The photon energy is absorbed by the surrounding tissue and causes an instantaneous temperature increase. The ultrasound pulses are excited by the thermal expansion and received by the internal or external imaging array. Since the photon absorption rate is highly correlated with the optical properties of the tissue, and the optical properties of the tissue are temperature dependent, photoacoustic imaging is capable of revealing the 3D structure of the thermal dose distribution during ablation process.

Method 7: Reconstruct the Ablated Region Image by Acoustic Radiation Force Imaging (ARFI).

This imaging method is based on the acoustic radiation force (ARF) effect. The HIFU transducer works as an ARF generator, which fires a high energy ultrasound beam to the tissue. Because of the discontinuity of mechanical property at the interface of treated and untreated tissue, the high energy ultrasound beam will apply a net force to the boundary and cause spatial movement. The imaging array performs the conventional ultrasound imaging during the entire process to capture the tissue boundary displacement. In contrast to conventional ARFI methods, this approach triggers the ARF pulse at the center of the interested region, and the pulse propagates along exactly the same beam path as the HIFU beam, regardless the acoustic impedance distribution of the tissue. This internal trigger and auto-alignment feature can provide unique advantages for the image reconstruction.

Method 8: Reconstruct the Ablated Region Image by Shear Wave Imaging (SWI).

This imaging method is based on the fact that ablated tissue has much higher stiffness than the normal tissue. The propagation speed and attenuation coefficient of shear wave (S-wave or elastic S-wave) is highly correlated with the medium stiffness. In our approach, shear wave is generated by sending high intensity ultrasound waves from the transducer attached to the interventional ablation catheter. The ARF pushes the tissue and generates shear wave, which sweeps across the ROI. An internal or external imaging array begins to fire imaging pulses once the shear wave is generated, and receive the echo signal. The wave front of the shear wave can be revealed by performing the elastography algorithm. The local tissue stiffness can be calculated by tracking the shear wave front propagation.

Method 9: Femtosecond Laser Photoacoustic Imaging

In another embodiment, the ultrasound transmitter 104 is a photoacoustic ultrasound transmitter that includes a femtosecond-pulsed laser. Compared to nanosecond (ns) lasers, which is the most used laser source in photoacoustic imaging, femtosecond (fs) lasers have higher pulse repetition rate and broader spectrum. According to previous studies, femtosecond lasers have higher photoacoustic generation efficiency than nanosecond lasers. In some embodiments, the ultrasound transmitter 104 can further include a photoabsorptive component arranged in an optical path of light from the femtosecond-pulsed laser.

Method 10: Continuous Wave Photoacoustic Imaging, Using High Repetition Rate Pulsed Laser Systems or CW Laser Systems In another embodiment, the ultrasound transmitter 104 is a photoacoustic ultrasound transmitter that includes a modulated laser that provides an encoded photoacoustic signal. The laser can be a pulsed or continuous wave laser.

In most medical ultrasound imaging configurations, the transducer fires a single ultrasound pulse, and waits until the sound echo is dissipated to fire the next pulse. This method limits the imaging pulse firing rate to KHz range. In medical photoacoustic imaging, low firing rate means that in order to get the desired image quality, the laser has to be able to provide a high energy per pulse so the data accumulation time won't be too long. In the current photoacoustic research, Q-switched lasers are mostly used to fulfill these requirements. However, these lasers are bulky, expensive, and more importantly, its high pulse peak power is dangerous for most medical applications. Compared to conventional nanosecond Q-switch lasers, diode lasers are low cost, more compact, and capable of firing with high repetition rate. The pulse peak power is in the hundreds-of-Watts range, which is much lower than the Q-switch lasers ($10^4$ to $10^6$ Watts). Since the pulse energy is much lower and the single shot photoacoustic signal is weak, more image frames need to be acquired in order to get the desired SNR. In this case, photoacoustic pulses will be fired right after the previous ones. To differentiate the echoes from different photoacoustic pulses, the laser pulses can be digitally encoded. If the coding base is large enough, the encoded pulses can be differentiated on the receiver side.

Method 11: Continuous Wave Scanning Photoacoustic Imaging

In another embodiment, the ultrasound transmitter 104 is a photoacoustic ultrasound transmitter that includes a continuous wave laser and a beam scanning assembly. Typically, photoacoustic generation requires pulsed light sources. However, with continuous lasers, if the laser is focused to a small region, and scanned over an area, for each point in this area, the laser illumination is equivalent to a pulsed laser. By using this approach, one or multiple scanning CW laser spots can be used for photoacoustic imaging. By varying the scan pattern and timing, the photoacoustic beam can be steered or focused.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An interventional system with real-time ablation thermal dose monitoring, comprising:
   an ultrasound transmitter configured to be arranged proximate a region of tissue while undergoing an ablation procedure;
   an ultrasound receiver configured to be arranged proximate the region of tissue such that the region of tissue is between the ultrasound transmitter and the ultrasound receiver,
   the ultrasound receiver being further configured to receive ultrasound signals from the ultrasound transmitter after transmission through the region of tissue and to provide detection signals; and
   a signal processing system configured to communicate with the ultrasound transmitter to obtain information concerning ultrasound pulse transmission times,
   the signal processing system configured to communicate with the ultrasound receiver to receive the detection signals and to calculate, based on the detection signals, a thermal dose delivered to the region of tissue in real time during the ablation procedure,
   wherein the ultrasound receiver provides information concerning reference detection times of pulses with known transmission times and provides corresponding detection times of detection signals from a thermal ablation zone of a tissue, and
   wherein the signal processing system is configured to calculate the thermal dose based on time of flight information using the reference detection times and based on time of flight information using the corresponding detection times of the detection signals from the thermal ablation zone.

2. The interventional system according to claim 1, further comprising:
   an ultrasound probe,
   wherein the ultrasound receiver is incorporated into the ultrasound probe so as to be acoustically coupled to an exterior surface of a body undergoing the ablation procedure.

3. The interventional system according to claim 2, wherein the ultrasound receiver comprises at least one of a linear or phased imaging array.

4. The interventional system according to claim 1, further comprising:
   an interventional tool,
   wherein one of the ultrasound receiver and the ultrasound transmitter is at least one of attached to or integral with the interventional tool.

5. The interventional system according to claim 4, wherein the ultrasound receiver comprises at least one of a linear or phased imaging array.

6. The interventional system according to claim 4, wherein the ultrasound transmitter and the ultrasound receiver comprise common transducer elements for transmission and reception.

7. The interventional system according to claim 4, wherein the interventional tool is an interventional tool adapted to be used in conjunction with an ablation tool.

8. The interventional system according to claim 4, wherein the interventional tool is an interventional ablation tool.

9. The interventional system according to claim 8, wherein the interventional ablation tool and the ultrasound transmitter share at least some common components to provide dual effects of ultrasound transmission and ablation.

10. The interventional system according to claim 8, wherein the interventional ablation tool is at least one of:
    a radio frequency,
    laser,
    high-intensity focused ultrasound, or
    thermal ablation tool.

11. The interventional system according to claim 2, wherein the signal processing system is configured to calculate the thermal dose delivered to the region of tissue in real time based on time of flight measurements of ultrasound signals from the ultrasound transmitter that pass through regions undergoing ablation as well as regions immediately surrounding the regions undergoing ablation.

12. The interventional system according to claim 1, wherein the signal processing system is configure to retrieve reference data corresponding to the region of tissue prior to the thermal dose and to calculate the thermal dose delivered to the region of tissue in real time based on a comparison of the reference data to detection signals.

13. The interventional system according to claim 12, wherein the reference data is intra-operatively acquired reference data.

14. The interventional system according to claim 12, wherein the reference data is at least one of based on a model or based on pre-operative data.

15. The interventional system according to claim 1, wherein the signal processing system is configured to calculate the thermal dose delivered to the region of tissue in real time based on a dispersion of the ultrasound signals from the ultrasound transmitter after transmission through the region of tissue.

16. The interventional system according to claim 8, wherein the interventional ablation tool is high-intensity focused ultrasound (HIFU) ablation tool that is further configured to provide acoustic pulses for imaging by an acoustic radiation force (ARF) effect, and wherein the signal processing system is configured to calculate the thermal dose delivered to the region of tissue in real time based on the ARF effect.

17. The interventional system according to claim 16, wherein the signal processing system is further configured to calculate the thermal dose delivered to the region of tissue in real time based on shear waves produced by the ARF effect.

18. The interventional system according to claim 8, wherein the ultrasound transmitter is a photoacoustic ultrasound transmitter comprising a femtosecond-pulsed laser.

19. The interventional system according to claim 18, wherein the ultrasound transmitter further comprises a photoabsorptive component arranged in an optical path of light from the femtosecond-pulsed laser.

20. The interventional system according to claim 8, wherein the ultrasound transmitter is a photoacoustic ultrasound transmitter comprising a modulated pulsed laser that provides an encoded photoacoustic signal.

21. The interventional system according to claim 8, wherein the ultrasound transmitter is a photoacoustic ultrasound transmitter comprising a continuous wave laser.

22. An ultrasound transmitter of an interventional tool, the ultrasound transmitter, comprising:
   a liquid cell for securing to the interventional tool;
   an optical fiber having a transmitting end coupled to the liquid cell such that the transmitting end is fixed within an interior space defined by the liquid cell, the interior space containing a fluid; and
   a laser optically coupled to the optical fiber, the optical fiber being configured to propagate a laser beam generated by the laser to the transmitting end of the optical fiber,
   wherein the fluid is selected to absorb the laser beam generated by the laser at the transmitting end of the optical fiber and wherein the liquid cell comprises an expandable portion that is free to expand and transmit acoustic energy generated by the fluid due to thermal expansion and phase change of the fluid when contained within the liquid cell and while the fluid is being exposed to energy from the laser beam to induce a Giant Photo-Acoustic Effect of the fluid and generate the acoustic energy.

23. The ultrasound transmitter according to claim 22, wherein the expandable portion is a rubber film substantially of a semispherical shape.

24. An interventional system with real-time ablation thermal dose monitoring, comprising:
   an interventional tool including an ultrasound transmitter configured to be arranged proximate a region of tissue while undergoing an ablation procedure, wherein the ultrasound transmitter comprises:
      a liquid cell including a fluid containing a suspension of carbon particles; and
      an optical fiber having a transmitting end coupled to the liquid cell such that the transmitting end is fixed within an interior space defined by the liquid cell, wherein the optical fiber is configured to be optically coupled to a laser, the optical fiber being configured to propagate a laser beam generated by the laser to the transmitting end of the optical fiber,
      wherein the fluid is selected to absorb the laser beam generated by the laser at the transmitting end of the optical fiber and wherein the liquid cell comprises an expandable portion that is free to expand and transmit acoustic energy generated by the fluid due to thermal expansion and phase change of the fluid when contained within the liquid cell and while the fluid is being exposed to energy from the laser beam to induce a Giant Photo-Acoustic Effect of the fluid and generate the acoustic energy;
   an ultrasound receiver configured to be arranged proximate the region of tissue such that the region of tissue is between the ultrasound transmitter and the ultrasound receiver, the ultrasound receiver being further configured to receive ultrasound signals from the ultrasound transmitter after transmission through the region of tissue; and
   a signal processing system configured to communicate with the ultrasound transmitter to obtain information concerning ultrasound pulse transmission times, and the signal processing system configured to communicate with the ultrasound receiver to receive the detection signals and to calculate, based on the detection signals, a thermal dose delivered to the region of tissue in real time during the ablation procedure,
   wherein the ultrasound receiver provides information concerning reference detection times of pulses with known transmission times and provides corresponding detection times of detection signals from a thermal ablation zone of a tissue, and
   wherein the signal processing system is configured to calculate the thermal dose based on time of flight information using the reference detection times and based on time of flight information using the corresponding detection times of the detection signals from the thermal ablation zone.

* * * * *